US008873703B2

(12) United States Patent
Ruimi et al.

(10) Patent No.: US 8,873,703 B2
(45) Date of Patent: *Oct. 28, 2014

(54) X RAY IMAGING SYSTEM WITH SCATTER RADIATION CORRECTION AND METHOD OF USING SAME

(75) Inventors: David Ruimi, Ganot Hadar (IL); Olga Shapiro, Haifa (IL); Ehud Dafni, Caesarea (IL)

(73) Assignee: Arineta Ltd., Caesarea (IL)

( * ) Notice: Subject to any disclaimer, the term of this patent is extended or adjusted under 35 U.S.C. 154(b) by 943 days.

This patent is subject to a terminal disclaimer.

(21) Appl. No.: 12/991,676

(22) PCT Filed: May 7, 2009

(86) PCT No.: PCT/IL2009/000470

§ 371 (c)(1), (2), (4) Date: Nov. 8, 2010

(87) PCT Pub. No.: WO2009/136400

PCT Pub. Date: Nov. 12, 2009

(65) Prior Publication Data

US 2011/0064190 A1 Mar. 17, 2011

Related U.S. Application Data

(60) Provisional application No. 61/126,747, filed on May 8, 2008.

(51) Int. Cl.
*A61B 6/03* (2006.01)
*G01T 1/29* (2006.01)
*A61B 6/00* (2006.01)

(52) U.S. Cl.
CPC ............ *G01T 1/2985* (2013.01); *A61B 6/4291* (2013.01); *A61B 6/032* (2013.01); *A61B 6/4028* (2013.01); *A61B 6/5282* (2013.01)
USPC .... 378/7; 378/9; 378/19; 378/87; 250/370.09

(58) Field of Classification Search
USPC ................ 378/6, 7, 9, 19, 87, 154, 155, 207; 250/370.09
See application file for complete search history.

(56) References Cited

U.S. PATENT DOCUMENTS 4,149,080 A * 4/1979 Schittenhelm .................... 378/7
4,995,107 A * 2/1991 Klingenbeck ..................... 378/7
5,594,772 A * 1/1997 Toki et al. ..................... 378/114
5,666,395 A * 9/1997 Tsukamoto et al. ......... 378/98.4
5,684,855 A * 11/1997 Aradate et al. .................... 378/4
5,771,269 A * 6/1998 Chao ................................ 378/5
6,054,712 A * 4/2000 Komardin et al. ....... 250/363.06
6,298,109 B1 10/2001 Ergun et al.
6,339,636 B1 * 1/2002 Ogawa .......................... 378/146
6,470,067 B1 * 10/2002 Harding .......................... 378/19
6,639,964 B2 * 10/2003 Schneider et al. ................ 378/7

(Continued)

*Primary Examiner* — Allen C. Ho

(74) *Attorney, Agent, or Firm* — William H. Dippert; Eckert Seamans Cherin & Mellott, LLC

(57) ABSTRACT

A CT scanner with scatter correction device and a method for scatter correction are provided. The method comprises positioning shields for shielding some of the CT detector elements from direct X ray radiation, while allowing scattered radiation to arrive at said shielded elements; measuring scatter signals from said shielded elements, indicative of scattered radiation intensity; and correcting for scatter by subtracting scatter intensity values estimated from said measured scatter signals from signals measured by unshielded detector elements.

41 Claims, 11 Drawing Sheets

102
104
200
110
111
222
220
226
219
218
208
Z direction

(56) References Cited

U.S. PATENT DOCUMENTS 6,839,401 B2 * 1/2005 Nokita .............................. 378/7
6,876,718 B2 * 4/2005 Tang .............................. 378/7
6,876,719 B2 * 4/2005 Ozaki .............................. 378/7
6,895,080 B2 * 5/2005 Baba et al. .................... 378/154
6,914,959 B2 * 7/2005 Bailey et al. .................... 378/65
6,925,140 B2 * 8/2005 Bruder .............................. 378/4
6,934,354 B2 8/2005 Hoffman
7,085,343 B2 8/2006 Shinno et al.
7,236,560 B2 * 6/2007 Malamud .............................. 378/7
7,260,171 B1 * 8/2007 Arenson et al. ................. 378/16
7,330,531 B1 2/2008 Karellas
7,366,279 B2 * 4/2008 Edic et al. ......................... 378/7
7,474,728 B2 * 1/2009 Schlomka et al. ................ 378/6
7,535,987 B2 * 5/2009 Matsuda .......................... 378/7
7,542,540 B2 * 6/2009 Matsuda .......................... 378/7
7,809,110 B2 * 10/2010 Ueki .............................. 378/98
7,920,672 B2 * 4/2011 Timmer et al. ................... 378/7
8,009,794 B2 * 8/2011 Partain .............................. 378/7
8,077,826 B2 * 12/2011 Ruimi et al. ...................... 378/7
8,199,873 B2 * 6/2012 Star-Lack et al. ................. 378/7
8,326,011 B2 * 12/2012 Star-Lack et al. ............. 382/131
2007/0205367 A1 9/2007 Deman et al.

* cited by examiner

X RAY IMAGING SYSTEM WITH SCATTER RADIATION CORRECTION AND METHOD OF USING SAME

CROSS REFERENCE TO RELATED APPLICATIONS

This application is based upon and claims the priority of PCT/IL2009/000470, filed May 7, 2009, and U.S. Provisional Application No. 61/126,747, filed May 8, 2008, both of which are incorporated herein in their entirety.

FIELD OF THE INVENTION

The present invention relates to X ray imaging. More specifically, it relates to measurement and compensation of scattered radiation in wide beam CT scanners, digital radiography, fluoroscopy and other digital X Ray imaging systems.

BACKGROUND OF THE INVENTION

Scatter radiation reduction and correction are required for both medical and nonmedical X ray imaging applications. Due to scattered x-ray photons, the local contrast, Signal to Noise (SNR) and the data accuracy are deteriorated. Various methods to reduce and compensate for the scattering effect have been suggested and had being used. Considering Computerized Tomography (CT) imaging, for example, early CT scanners have used narrow fan beams and were assisted by antiscatter grids so scatter radiation was not a major issue in these systems. However, in modern CT scanners, large area X-ray detectors having a plurality of detector element arranged in rows and columns are used to perform multi-slice imaging. In these systems the width of a beam is significantly larger than in earlier single slice CT. Accordingly; the adverse effect of scattering is intensified.

In U.S. Pat. No. 5,666,391 to B. Ohnesorge, et al. (Sep. 9, 1997) the inventors suggest to correct for the scattered radiation by calculating a theoretical scattering distribution, based on the subject contour and shape as reconstructed from the data before the correction is applied, and subtracting the calculated scattering data from the actual collected data.

In U.S. Pat. No. 6,618,466 to N. Ruola (Sep. 9, 2003) the inventor suggests positioning an array of shields between the radiation source and the scanned subject, acquiring some views of the subject from some angels wherein the shielded areas of the detector are used to measure the scattered radiation, removing the shields array and scanning the subject without the array. The data collected in the first scan is used to calculate the scattering by interpolation for the entire array for all view angles and then to correct the data of the second scan.

In U.S. Pat. No. 7,336,759 to N. Masatak (Feb. 26, 2008) the inventor suggests collecting in addition to the wide beam scan data to be corrected, an additional set of projection data with narrow beam. The data with narrow beam is used to assess the effect of the scattered radiation at the same projections angles, and from these measurements to interpolate the scattering distribution of the wide beam.

However, none of these methods provides a solution for accurate measurement and compensation for the scattered radiation without adding steps to the imaging procedure and without exposing the subject to additional radiation.

SUMMARY OF THE INVENTION

The present invention relates to X ray imaging. More specifically, it relates to measurement and compensation of scattered radiation in wide beam CT scanners, digital radiography, fluoroscopy and other digital X Ray imaging systems.

Accordingly, an object of the present invention is to provide an apparatus and a method of measuring the radiation scatter in the CT system and other digital X ray imaging systems, during the imaging of a subject, and compensating for the scattered radiation effects.

A feature of the invention is the measurement of scattered radiation through use of radiation opaque shields placed in the imaging system during the acquisition whereby substantially only scattered radiation is received by so shielded areas of the detector. The scattered radiation for the entire detectors matrix can then be interpolated from the measured scattered radiation in the shielded detector parts and can be subtracted from the measured data.

It is therefore provided in accordance with a preferred embodiment of the present invention, a method for imaging a subject while correcting for scattered radiation scattered from said subject, the method comprising:

a. providing at least a first source of X ray radiation, a detector for the X ray radiation, and a plurality of radiation shields, said radiation shields positioned between the source and the detector;
b. irradiating the subject by said first X ray source and acquiring X ray data from said detector, wherein X rays received by said detector comprise: direct radiation from the source that was attenuated by said subject; and scattered radiation that was scattered by said subject, and wherein shielded parts of the detector area shaded by said shields such that said shielded parts are irresponsive to direct radiation and responsive to scattered radiation, and wherein un-shielded parts of the detector area are irresponsive to direct radiation and to scattered radiation;
c. correcting the data received by said un-shielded parts of the detector area, wherein said correction is based on scattered radiation data received by said shielded parts of the detector area.

Furthermore and in accordance with another preferred embodiment of the present invention, the method further comprises correcting the data received by said shielded parts of said detector, wherein said correction is based on direct radiation data received by said un-shielded parts of the detector.

Furthermore and in accordance with another preferred embodiment of the present invention, said first X ray source, said detector, and said shields are mounted on a rotating frame and operative for computer tomography imaging of said subject.

Furthermore and in accordance with another preferred embodiment of the present invention, wherein scatter correction is applied to multiple X ray projection data, each projection data acquired at a different one of multiple rotation angles.

Furthermore and in accordance with another preferred embodiment of the present invention, wherein said X ray source, said detector and said shields are used for a fluoroscopic imaging of said subject.

Furthermore and in accordance with another preferred embodiment of the present invention, wherein said detector is pixilated to detector elements and said shields comprise elements of radiation opaque material blocking substantially all direct radiation from reaching shielded detector elements.

Furthermore and in accordance with another preferred embodiment of the present invention, wherein said detector is pixilated to detector elements and said shields comprise radiation opaque material blocking substantially all direct radiation from reaching a part of the active area of partially shielded detector elements.

Furthermore and in accordance with another preferred embodiment of the present invention, wherein said shields are operable to move out of the beam path during a calibration process of said detector, and move into the beam path during imaging of said subject.

Furthermore and in accordance with another preferred embodiment of the present invention, further providing an anti-scatter grid adjacent to said detector and wherein said shields are positioned adjacent to said anti-scatter grid.

Furthermore and in accordance with another preferred embodiment of the present invention, wherein said anti-scatter grid is adjacent to said detector and said shields are positioned at a distance from the antiscatter grid, posterior to said subject.

Furthermore and in accordance with another preferred embodiment of the present invention, wherein said shields are positioned at a distance from said detector face, posterior to said subject.

Furthermore and in accordance with another preferred embodiment of the present invention, further providing a second X ray source, displaced from said first X ray source, wherein said first and said second X ray sources are operable to irradiate a common area of said detector, wherein said shields are operable to shield direct radiation from said first X ray source from reaching shielded parts of said detector, and wherein said shielded parts of said detector are capable to receive direct radiation from said second X ray source.

Furthermore and in accordance with another preferred embodiment of the present invention, wherein direct radiation received from said second X ray source is used for calibrating detector elements which are shielded by said shields from radiation emitted by said first X ray source.

Furthermore and in accordance with another preferred embodiment of the present invention, wherein the step of correcting the data received by said un-shielded parts of the detector area comprises:

a. calculating an amount of scattering received by detector elements from data acquired by said shielded parts of said detector; and
b. subtracting said calculated amount of scattering from the data acquired by said un-shielded parts of said detector.

Furthermore and in accordance with another preferred embodiment of the present invention, wherein the step of correcting the data received by said un-shielded parts of the detector area comprises fitting a scatter map for the detector area, based on the read out of said shielded parts of said detector.

Furthermore and in accordance with another preferred embodiment of the present invention, wherein the step of fitting a scatter map for the detector area comprises using a polynomial fitting function.

Furthermore and in accordance with another preferred embodiment of the present invention, wherein the step of fitting a scatter map for the detector area comprises performing spatial interpolation on read out of shielded parts of said detector.

Furthermore and in accordance with another preferred embodiment of the present invention, wherein the step of performing spatial interpolation comprises using cubic or higher order spline interpolation.

Furthermore and in accordance with another preferred embodiment of the present invention, wherein said first and said second X ray sources are operated sequentially.

Furthermore and in accordance with another preferred embodiment of the present invention, wherein the step of the scatter correction comprises correction of data acquired at one time based on scattered radiation measured at a different time.

Furthermore and in accordance with another preferred embodiment of the present invention, wherein the process of the scatter correction comprises averaging of scatter data measured by shielded parts of said detector over time.

Furthermore and in accordance with another preferred embodiment of the present invention, wherein the array of shields is operable to move between alternate positions during the calibration process such that parts of the detector which are shielded during subject imaging are not shielded during calibration.

The present invention further comprises in accordance with yet another preferred embodiment of the present invention a system for imaging a subject while correcting for scattered radiation, the system comprising:

a. At least a first source of X ray radiation;
b. a detector for detecting said X ray radiation;
c. an array of radiation shields, said array is positioned between said at least first source and said detector;
d. a controller configured for acquiring X ray data from said detector, wherein X rays received by said detector comprise direct radiation from the source that was attenuated by said subject and scattered radiation that was scattered by said subject, and wherein parts of the detector area shielded by the shields and are substantially irresponsive to said direct radiation and responsive to said scattered radiation;
e. an image processor configured for correcting the data received by parts of the detector area which are not shielded by said shields, wherein said correction is based on scattered radiation data received by parts of the detector area which are shielded by said shields.

Furthermore and in accordance with another preferred embodiment of the present invention, wherein said image processor further configured for correcting the data received by said parts of the detector which are shielded by said shields, wherein said correction is based on direct radiation data received by said parts of said detector which are not shielded by said shields.

Furthermore and in accordance with another preferred embodiment of the present invention, wherein said X ray source, said detector and said array of shields are mounted on a rotating frame and operative for computer tomography imaging of said subject.

Furthermore and in accordance with another preferred embodiment of the present invention, wherein scatter correction is applied to multiple X ray projection data, each projection data acquired at a different one of multiple rotation angles.

Furthermore and in accordance with another preferred embodiment of the present invention, wherein said X ray source, said detector and said array of shields are used for a single radiographic imaging of said subject.

Furthermore and in accordance with another preferred embodiment of the present invention, wherein said X ray source, said detector and said array of shields are used for fluoroscopic imaging of said subject.

Furthermore and in accordance with another preferred embodiment of the present invention, wherein said detector is pixilated to detector elements and said shields comprised of elements of radiation opaque material blocking substantially all direct radiation from reaching shielded detector elements.

Furthermore and in accordance with another preferred embodiment of the present invention, wherein said detector is pixilated to detector elements and said shields comprised of radiation opaque material blocking substantially all direct radiation from reaching a part of the active area of partially shielded detector elements.

Furthermore and in accordance with another preferred embodiment of the present invention, wherein said array of shields is operable to move out of the beam path during calibration process and move into the beam path during imaging of said subject.

Furthermore and in accordance with another preferred embodiment of the present invention, further comprises an anti-scatter grid positioned adjacent to said detector, wherein said shields comprising elements of radiation opaque material are positioned adjacent to said anti-scatter grid.

Furthermore and in accordance with another preferred embodiment of the present invention, further comprises an anti-scatter grid positioned adjacent to said detector and said shields comprising elements of radiation opaque material are positioned at a distance from said anti-scatter grid, posterior to the subject.

Furthermore and in accordance with another preferred embodiment of the present invention, said shields comprising elements of radiation opaque material are positioned at a distance from said detector's face, posterior to said subject.

Furthermore and in accordance with another preferred embodiment of the present invention, further comprises a second X ray source displaced from said first X ray source, wherein said first and said second X ray sources are operable to irradiate a common detector area, wherein shields are operable to shield direct radiation from said first X ray source from reaching shielded parts of said detector, said shielded parts capable of receiving direct radiation from said second X ray source.

Furthermore and in accordance with another preferred embodiment of the present invention, wherein direct radiation received from said first X ray source is used for calibrating said detector elements which are shielded by said shields from radiation emitted by a second X ray source.

Furthermore and in accordance with another preferred embodiment of the present invention, wherein data acquired by shielded detector elements is used to calculate an amount of scattering received said shielded detector elements and said calculated amount of scattering is subtracted from the data acquired by said detector elements.

Furthermore and in accordance with another preferred embodiment of the present invention, wherein said array of shields is operable to move between alternate positions during a calibration process such that parts of said detector which are shielded during imaging said subject are not shielded during calibration.

Furthermore and in accordance with another preferred embodiment of the present invention, wherein said array of shields is operable to move between at least first and second calibration positions during a calibration process such that parts of said detector which are shielded while said array of shields in said first calibration position are not shielded while said array of shields in said second calibration position.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

Figure 1A:
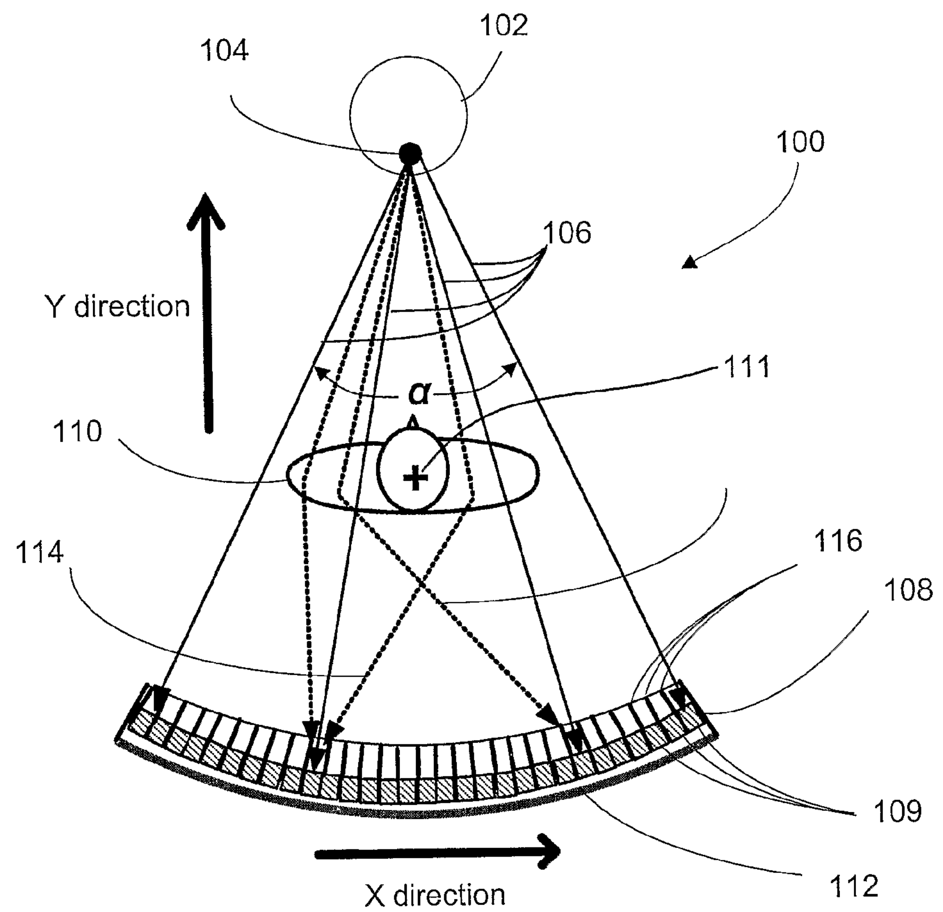
FIG. 1*a* schematically depicts a front view of prior art cone beam CT system.

The present invention relates to X ray imaging. More specifically, it relates to measurement and compensation of scattered radiation in wide beam CT scanners and other digital X Ray imaging systems.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In discussion of the various figures described herein below, like numbers refer to like parts.

The drawings are generally not to scale. For clarity, non-essential elements were omitted from some of the drawings.

The invention is described below in reference to CT systems as exemplary embodiments. However, the invention applies also the projection imaging systems and the geometries as well as the algorithms and procedures described herein below in reference to CT systems are applicable to projection imaging systems as well.

FIG. 1*a* schematically depicts a front view of prior art cone beam CT system.

Figure 1B:
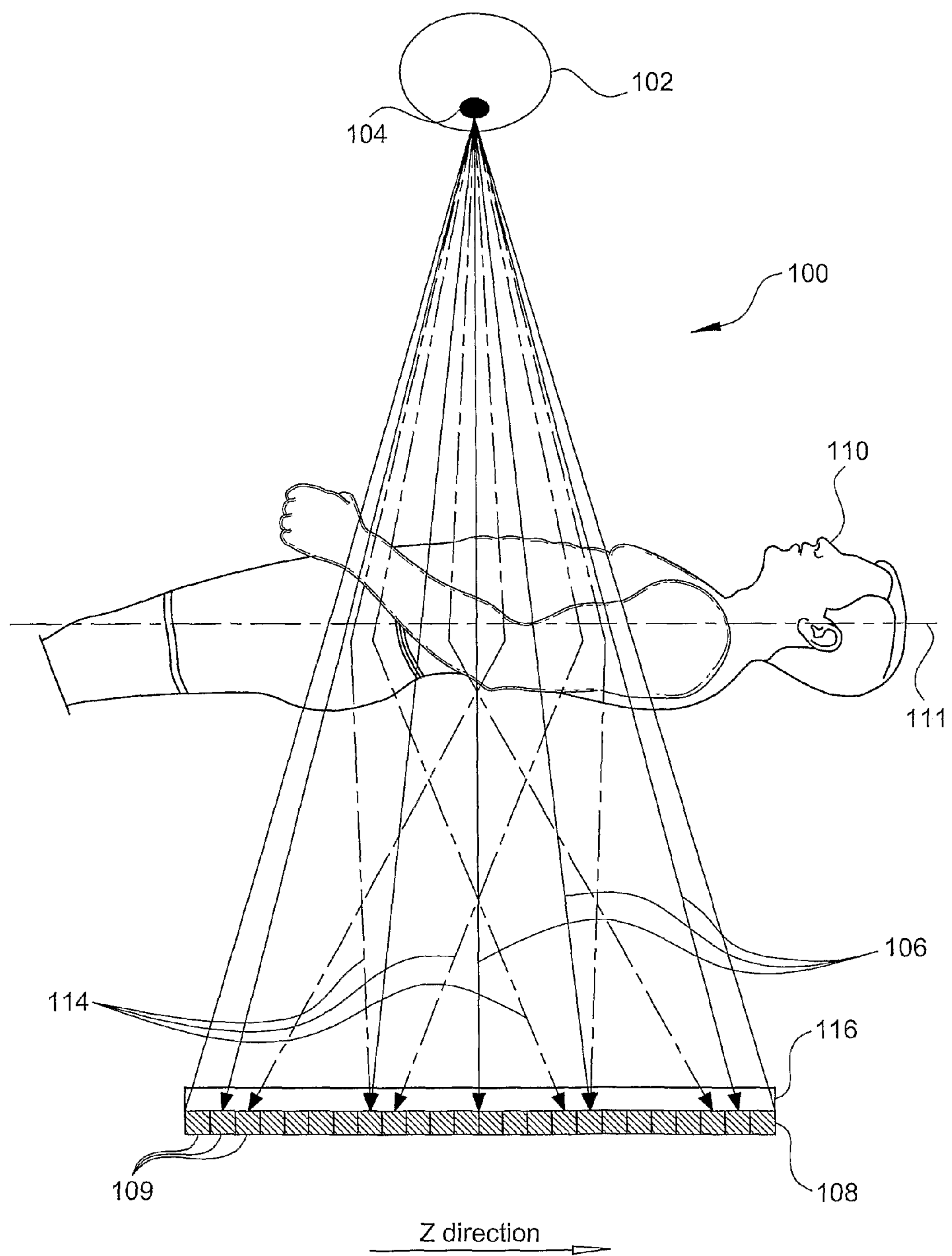
FIG. 1*b* schematically depicts a side view of prior art cone beam CT system.

FIG. 1*b* schematically depicts a side view of prior art cone beam CT system.

FIG. 1*a* (front view) and 1*b* (side view) illustrate a prior art cone beam CT scanner 100. X ray source 102 such as an X-Ray tube, with focal spot 104 emits a beam of X radiation (only a few radiation paths 106 (are shown for clarity) collimated to illuminate detector array 108. Typically the source-detector pair is mounted on a rotating gantry and a subject to be examined 110 is positioned between the source and the detector. Detector array 108 may be composed of an array of discrete detector elements 109 (only a few elements are marked for clarity) arranged in rows and columns, a flat panel detector or the like. It may have a spherical or arc shape centered about the focal spot (as shown), be planar or have other surface curvature. Herein below we refer to “rows ”of the detector as the X direction of the detector perpendicular to the rotation axis (Z direction).

Attenuation data for X rays 106 that have been emitted during the scan, attenuated by subject 110 and received by detector array 108 are acquired by dedicated electronic circuits 112. This data is transmitted to an image processor (not shown) and used for calculating the Linear Attenuation Coefficient (LAC) of their path through the subject and then, reconstructed to images by an algorithm selected from algorithms known in the art; said images are displayed and stored for further processing. CT scanning can be done in single acquisitions during rotation of the source and detector by at least 360° (referred to as full scan) or at least 180° (referred to as partial scan). Preferably, a partial scan is done by rotating the gantry by $180°+\alpha$, wherein $\alpha$ is the angular span of the cone beam about the center of rotation 111. Scanning can be done also with continuous rotation combined with subject translation (referred to as spiral or helical scan).

In the description of embodiments of the invention related o CT the following coordinate system is used: Z is parallel to the rotation axis 111, Y is pointing from the rotation axis 111 to the focal point of the X ray source 104, and X is tangent to the focal spot trajectory. The coordinate system is rotating with the gantry frame.

Various parts of the CT scanner 100, including the gantry, subject support, data acquisition system, controllers, image processors, display unit and other parts are not shown in FIG. 1*a*, FIG. 1*b* and subsequent figures for clarity. A person skilled in the art will appreciate these parts are provided and included in the systems.

In FIGS. 1*a* and 1*b*, one may notice some X-rays such as represented by numeral 114 that, as a result of the interaction with the subject 110, had being scattered from their original direction, and impinged on detector elements that are not positioned in the direct path of the X ray as it was emitted from source 104. The scattered radiation intensity which is detected by the detector reduces the image contrast, increases the statistical noise, and results in various image artifacts. These artifacts results from detecting in a detector element 109 signals which are larger than the signal which would have been resulted without scattering. As a result, the data set may be inconsistent. Additionally, since the detected signal is larger, the estimated LAC may be smaller than the true value. In addition, the distribution of the scattered photons is highly dependent on the scattering subject. Therefore, scatter reduction and correction are required to improve reconstruction accuracy of LAC distribution for both medical (for example: human patient diagnostics, small animal imaging) and non-medical imaging applications (for example: explosive detection, nondestructive testing, industrial imagine guided manufacturing applications).

Much of the scattered radiation can be efficiently eliminated by using post-patient collimator, usually referred to as antiscatter grid, which limits each detector cell’s field of view to the vicinity of the x-ray focal spot. In prior art third generation fan beam CT scanners, the radiation beam is fan shaped. Reduction of scattering effects on the image can be accomplished relatively easily by employing a one dimensional array of collimator leafs marked in FIG. 1*a* and FIG. 1*b* by numerical 116 (only few are marked for clarity). Leafs 116 are positioned near the surface of the detector and are focused at the x-ray focal spot 104. Leafs 116 are commonly made of thin sheet of highly X ray absorbing material such as Tungsten or Tantalum.

One dimensional anti-scatter array of leafs 116 is efficient in rejecting radiation that was scattered azimuthally respective of the rotating gantry but it is not efficient in rejecting radiation scattered in a direction substantially along the detector columns (the columns defined being parallel to the rotation axis 111). Therefore, as demonstrated in FIG. 1*b*, in a wide beam CT (also called cone beam CT) with a one dimensional antiscatter array, significantly more scattered radiation is detected by each detector element 109 than in a narrow beam CT. One solution to reduce scatter radiation level is to provide a two dimensional antiscatter grid near the surface of the detectors. This solution is mechanically complicated and expensive.

The aim of this invention is to suggest a method to measure and correct for the scattered radiation during a CT scan or other digital X ray imaging procedures.

Figure 2A:
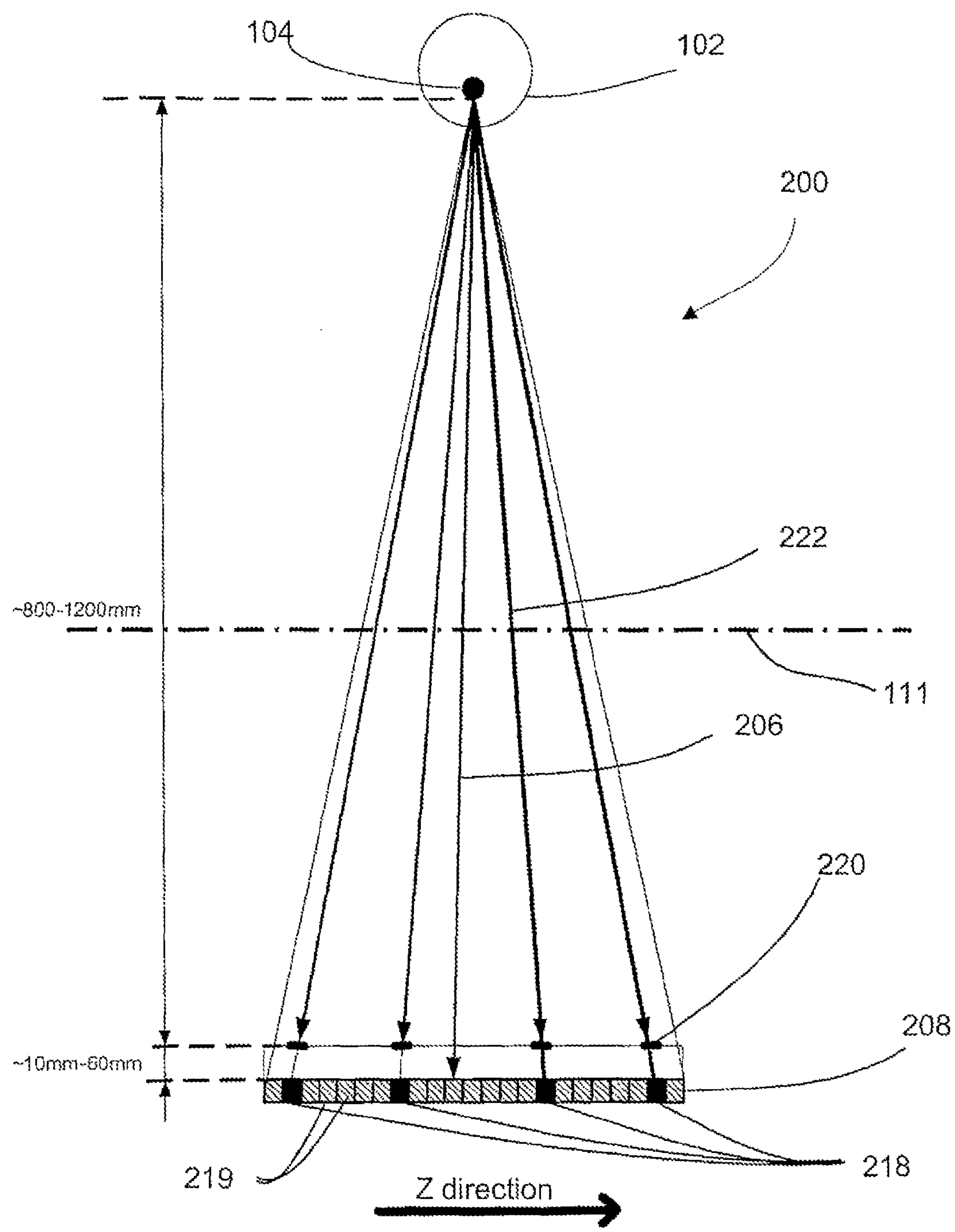
FIG. 2*a* is an illustration of a side view of CT system 200 in absent of imaged subject, according to an exemplary embodiment of the present invention.

FIG. 2*a* is an illustration of a side view of CT system 200 in absent of imaged subject, according to an exemplary embodiment of the present invention.

Detector array 208 is shown to be pixilated to detector elements 219 (It should be noted that detector array 208 comprises a 2D array of detector elements 219 in X and Z directions; only a few detector elements 219 are marked for clarity. The number of pixels in the detector array may be larger than that depicted in these figures.) A particular sub-set of detector elements 218 are shaded by radiation opaque shields 220 that block direct (un-scattered) X-ray radiation 222 from being received by the detector. (In this drawing, four elements 218 are seen, darkly colored. Elements 218 may be of different, similar or preferably identical construction to the other elements in the array. The number of detector elements 218 may be different than four for each column of detector array 208. Optionally, some columns have shaded detector elements and some do not. Optionally, detector elements belonging to different columns are shaded in different rows. Optionally, same shield 220 may block radiation to a plurality of adjacent detector elements 218.)

In embodiments of the present invention shields 220 are preferably distributed over the entire detector array 208 operable for imaging the subject 110. Preferably, about 0.5% to 1% of the detector elements 219 are shaded although as little as 0.1% or less or as much as 5% or more of the detector elements may be shaded.

If the detector array 208 is irradiated without the presence or a scanned subject or other scattering body, the parts of the detector which are not shaded by shields receive the direct radiation 206 from the source 102, whereas the parts of the detector array which are shaded receive substantially no radiation at all. System 200 and other embodiments described herein below have a controller operable to irradiate the patient, control motion of the gantry and the subject's support and acquire data from the detector. Further, they have an image processor operable to process the acquired data as described hereinbelow.

Figure 2B:
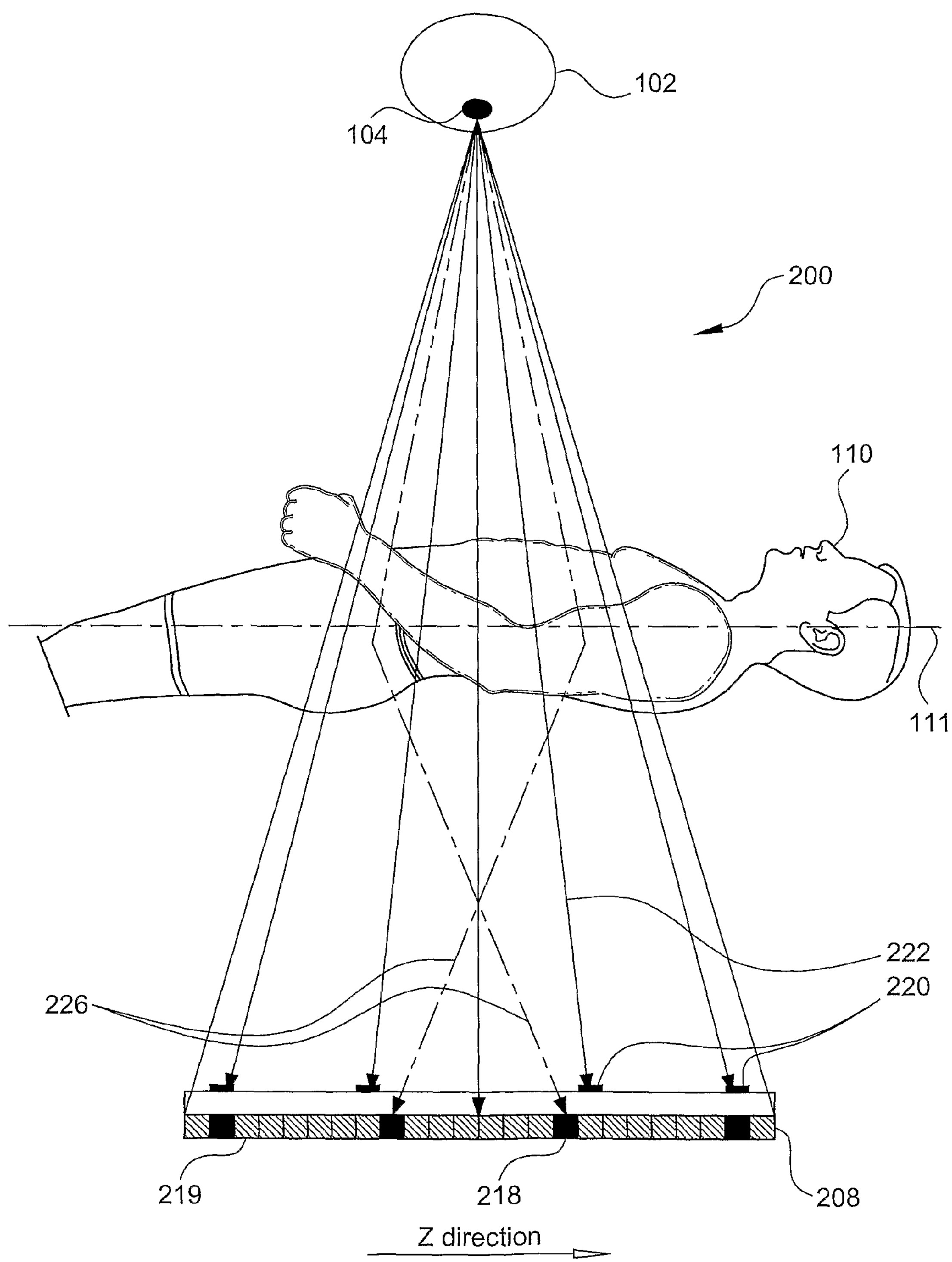
FIG. 2*b* is an illustration of a side view of CT system 200 in presence of imaged subject 110, according to an exemplary embodiment of the present invention.

FIG. 2*b* is an illustration of a side view of CT system 200 in presence of imaged subject 110, according to an exemplary embodiment of the present invention.

For clarity, some elements marked in FIG.2*a* are un-marked in FIG. 2*b*. As illustrated in FIG. 2*b*, during scan of a subject 110, radiation is being scattered by the subject and impinges on the shaded parts of the detector, as shown for example, for the scattered X ray marked by numeral 226. Therefore, the shaded parts 218 of the detector array 208 are operative to measure the amount of scattered radiation.

Figure 3A:
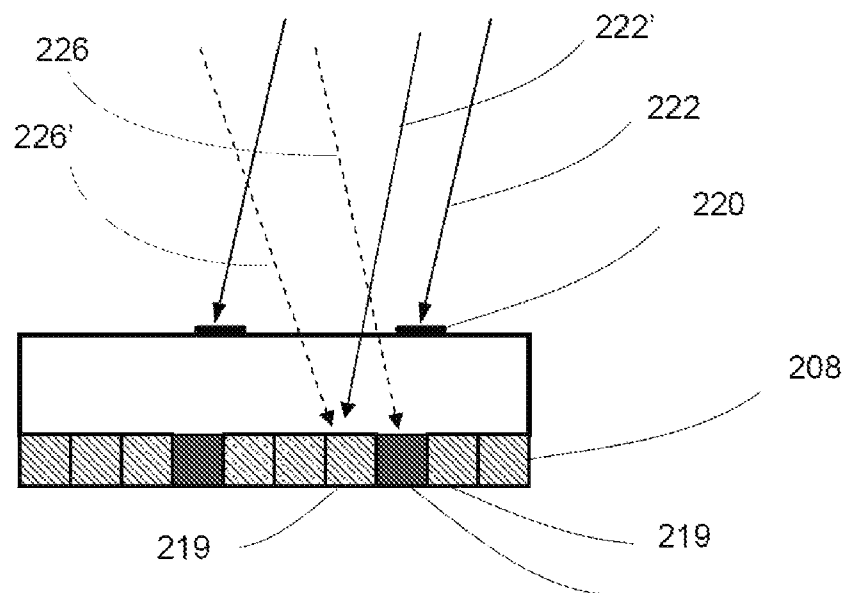
FIG. 3*a* schematically depicts a "zoom in" display of a column of detector elements in an exemplary embodiment of the invention wherein a detector element is fully shaded by a shield that blocks substantially all the direct radiation.

FIG. 3*a* schematically depicts a "zoom in" display of a column of detector elements in an exemplary embodiment of the invention wherein detector element 218 is fully shaded by shield 220 that blocks substantially all the direct radiation 222 from the focal spot 104 to the detector element 218. Shield 220 may comprise a of heavy metal such as tungsten or tungsten alloy or of other material known in the art as an efficient X ray absorber such as lead or tantalum. Shield 220 may have a thickness of 1 mm or 2 mm or other value in the direction of the direct beam and area corresponding to the area of the shaded detector element. Preferably, the thickness of shield 220 is selected such that the attenuation of the shield to X ray emitted by X ray source 102 is substantial. For example, transmission of the direct beam 222 through shield 220 is less than 1%. Optionally, higher attenuation is selected. The thickness of shield 220 may be selected depending on the material used for the shield and the X ray energy range used, as attenuation depends on both. Optionally, attenuation of shield 220 is selected such that the direct radiation 222 which penetrates through the shield is comparable or preferably substantially smaller than the typical scattered radiation which may be scattered onto the shaded detector element 218 when a typical subject is imaged. The shield 220 may he positioned between 40 mm to 60 mm from, the detector element 208 surface although lower or higher values are also possible. Optionally, the gap between shield 222 and the surface of detector element 218 is determined according to system geometry and the size of detector elements 218. The gap between shield 222 and the surface of detector element 218 allows scattered beams 226 to reach the shaded detector element 218.

It should be noted that direct radiation 222 is blocked by shield 220, and cannot arrive at detector element 218. In contrast, unshielded detector element 219, in the neighborhood of shielded detector element 218, receives both direct radiation 222' and scattered radiation 226'. Scattered radiation is statistically similar in neighboring and close-by elements. Thus scattered radiation 226', detected together with direct radiation 222' on detector element 219, may be estimated from the radiation 226 detected by shielded detector element 218.

Figure 3B:
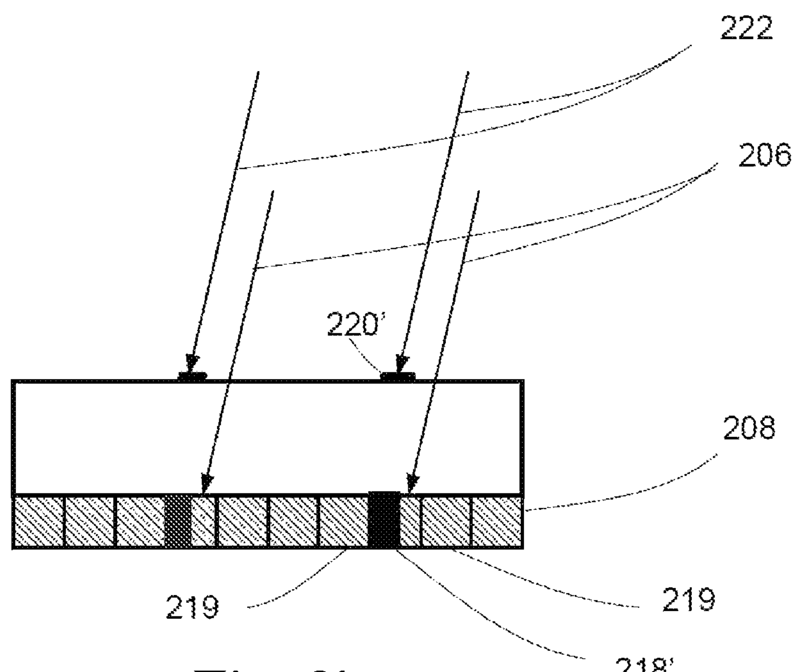
FIG. 3*b* schematically depicts a "zoom in" display of detector elements in an embodiment of the invention wherein a detector element is only partially shaded by a shield.

FIG. 3*b* schematically depicts a "zoom in" display of detector elements in an embodiment of the invention wherein detector element 218' is only partially shaded by shield 220', that blocks part (for example: about 50%) of the direct radiation 222 from the focal spot 104 to the detector element 218'. In this figure, the shaded section of detector element 218' is darkened. A direct, un-blocked x-ray 206 is also displayed. This arrangement eases the positioning of the shields respective the designated detector elements and reduces the risk of shading other detector elements. Another advantage of partial shadowing is that enable calibration of the partially shaded detector elements 218' without moving the shields 220', as described further below.

Pixilated X ray detectors as described herein compose of multiple elements arranged in rows and columns, each connected to data acquisition circuit. As known in the art, the readings of the detector elements are corrected for the different gain of each element's readout circuit, as well as possible differences between detector elements in geometrical efficiency and in the un-attenuated (without scanned subject) radiation intensity impinging on the elements. This is typically done by operating the scanner to acquire data without a scanned subject or with known homogeneous absorber, storing the calibration data and using it for normalizing the data acquired with a scanned subject. The procedure is referred at as "air calibration" or as "flat field calibration".

Referring now to FIG. 3*a*, in embodiments wherein a subset of the detector array elements such as element 218 are shaded from direct radiation, it is desired to perform the air calibration scan without shading these elements.

Figure 3C:
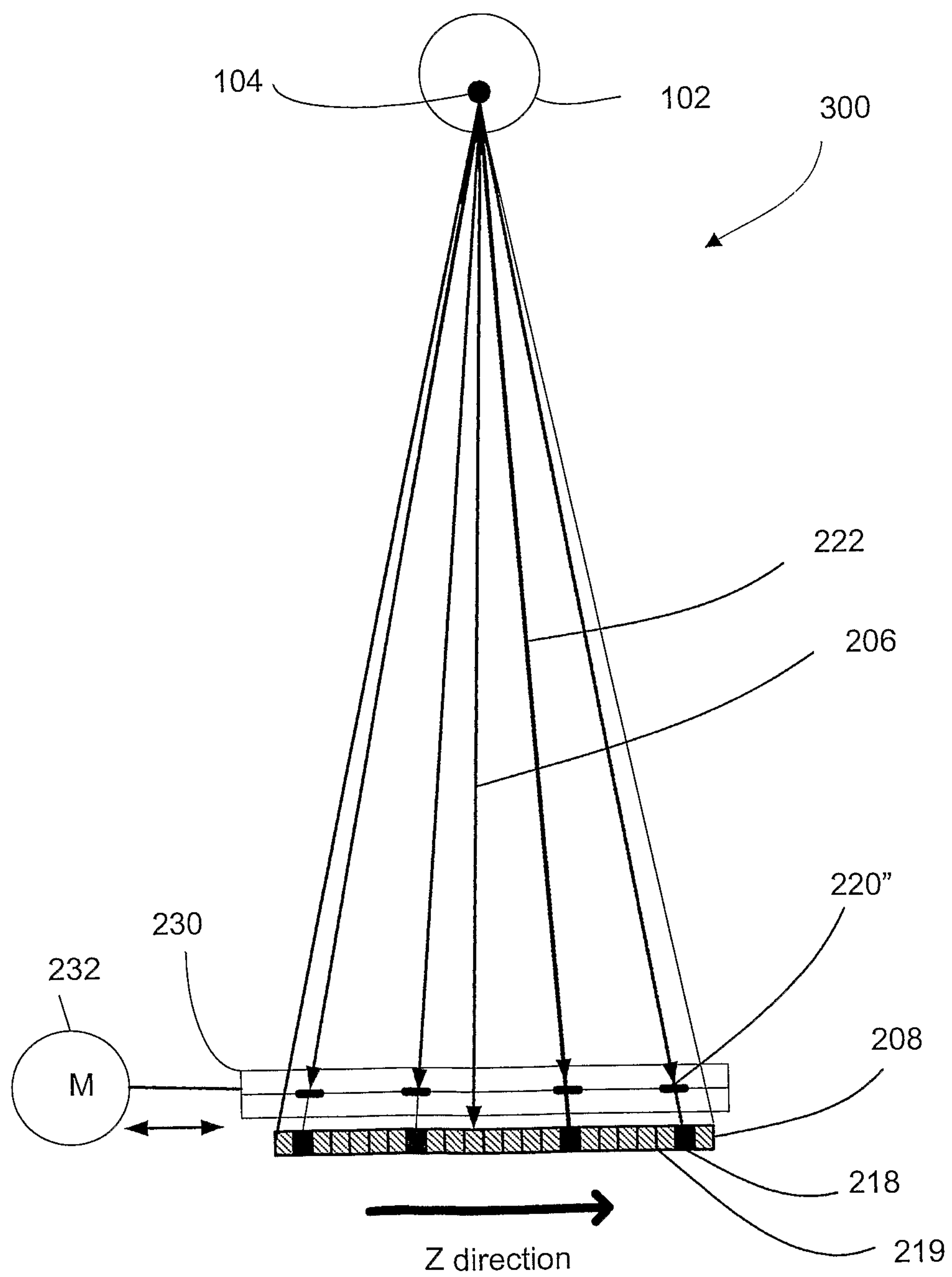
FIG. 3*c* is a schematic illustration of a side view of a CT system 300 according to an exemplary embodiment of the invention wherein radiation opaque shields are embedded in a radiation translucent carrier.

FIG. 3*c* is a schematic illustration of a side view of a CT system 300 according to an exemplary embodiment of the invention wherein radiation opaque shields 220" are embedded in a radiation translucent carrier 230. Carrier 230 may be composed of double layers of polycarbonate sheet, for example, 1 mm thick, mounted on metal support frame or other suitable materials known in the art. Carrier 230 is preferably mounted on linear rails (not shown) and is operable to be moved in the Z direction out of the beam path or be moved to a position wherein shields 220" shade designated detector elements (seen darkened in this figure). Carrier 230 motion is accomplished by motion drive and control system 232.

According to an exemplary embodiment of the invention, during air calibration of the system 300 in FIG. 3*c*, carrier 230 is moved out of the beam path. All elements of detector array 208 are then calibrated. During subsequent scan of a subject, carrier 230 is moved in, and the shaded detector elements 218 are operable to measure the scattered radiation.

According to another exemplary embodiment of the invention, during the first stage of air calibration of the system 300 in FIG. 3*c*, carrier 230 is moved to a first position. All fully exposed elements of detector array 208 are then calibrated.

During the second stage of air calibration of the system 300 in FIG. 3*c*, carrier 230 is moved to a second position, fully exposing detector elements that were fully or partially shielded during the first calibration stage. Elements that were shielded in first stage of air calibration may then be calibrated.

During subsequent scan of a subject, carrier 230 is moved to a known position, and the shaded detector elements are operable to measure the scattered radiation.

Considering now a given projection (data set acquired from the detector array at one rotation angle), wherein air calibration is obtained as described hereinabove in reference to FIG. 3c or by other methods described herein below and designated detector elements are completely shielded from direct radiation 206.

Let R(i,j) be the air calibration corrected raw data received by detector element at row i and column j in a subject scan, We denote R(i,j)=D(i,j)+S(i,j) wherein D(i,j) corresponds to direct radiation from the X ray source (that was attenuated by the subject) and S(i,j) corresponds to scattered radiation, Let (k,l) be a subset of (i,j) corresponding to detector elements which are shaded by shields. The same sub-array (k,l) is applicable for all projections of the scan at any gantry rotation angle, Then S(k,l)=R(k,l) is the scattered radiation at shaded detector element (k,l).

As known in the art, the intensity of the scattered radiation S(i,j) is a slow varying function along the rows and columns of the array, as compared to the fast variation observed frequently for the direct radiation function D(i,j). Therefore, the scattered radiation of the un-shaded detector elements can be determined by interpolation of the data S(k,l) from sub-set (k,l) to the entire set S(i,j). The interpolation in this step and in other steps and embodiments hereinbelow may be linear or preferably quadratic or higher order spline interpolation or by any other interpolation algorithm known in the art. Alternatively, a scatter map S(i,j) may be generated by a fit of a smooth function such as polynomial function to the S(k,l) data by methods known in the art.

The array S(i,j) obtained by said interpolation is subtracted from the array R(i, j) to yield the scatter corrected projection data for the un-shaded detector elements D(i, j):

$$D(i,j)=R(i,j)-S(i,j)$$

Further, the attenuation data D(k,l) that would have been received by the shaded elements if the shields 220 were not present are determined by interpolation of D(k,l) from the values D(i, j) of neighboring channels.

Finally, the scattered corrected direct radiation area for the entire array of un-shaded and shaded detectors elements is reconstructed to scattered corrected images by methods known in the art (for example Filtered Back Projection (FBP) or iterative reconstruction algorithms)

Considering now embodiments as illustrated in FIG. 3b wherein a fraction f of the active area of detector elements is shaded by shields 220'. f has a value larger than 0 and smaller than 1. In preferred embodiments f is about 0.5 although higher or lower values may be used as well. For simplicity it is assumed the same value of f is applied to all shaded detectors elements although different values of f (m) can be used for different shaded elements m.

In these embodiments the shields 220' are partially shading the corresponding detector elements during air calibration. Air calibration readings values are (1−f) times the readings that would have been received without the shields. During a subject scan, the direct radiation received by the shaded elements is reduced by (1−f) as well, wherein the scattered radiation is not reduced. Therefore, normalization of the measured data by the reduced air calibration data yields:

$$R(k,l)=D(k,l)+S(k,l)/(1-f)=D(k,l)+fS(k,l)/(1-f)$$

Wherein the normalized direct radiation component D(k, l) is the same as would be obtained without the shields and the normalized scattered radiation component S(k,l) is increased. For example, for f=0.5: R(k,l)=D(k,l)+2S(k,l)

The data is processed in the following way:

The values of D(k,l)+S(k,l) for the shaded detector elements are determined by interpolation of the measured values R(i,j) of un-shaded neighbors, The values of scattered radiation S(k,l) for the shaded detector elements are determined by subtraction of the interpolated results from measured results for the shaded elements and multiplication by (1−f)/f, The values of the scatter radiation S(i,j) for the un-shaded detector elements are determined by interpolation of the scattering S(k,l) of the shaded elements so achieved, to fit of a scatter map for most of the detector area. In order to achieve a fit of stable and smooth function to the relatively sparse scattering sampling points, a spatial spline interpolation (e.g. cubic or spline of higher order), or a convolution with a smooth kernel, could be used.

The direct radiation D(i,j) for the un-shaded detector elements is determined by subtraction of the interpolated scattered data from the raw data, The direct radiation D(k,l) for the shaded detector elements is determined by subtraction of the scattered data from the raw data (taking in account the 1/(1−f) factor) or by interpolation from the un-shaded neighbors.

Embodiments of the present invention are provided with a controller operable to carry out the scatter subtraction from the raw data using algorithms as described hereinabove. Persons experienced in the art will appreciate there are other algorithms to deduce the values of the direct and scattered radiation and subtract the scattered radiation. These algorithms are also covered by the invention in as much they use the data measured for the shaded and un-shaded detector elements to correct the data for the entire array. In particular, the air calibration data measured for the detector elements was described hereinabove to be applied both to the direct radiation and scattered radiation. Some algorithms may normalize the direct and scattered components in different ways.

In a CT systems, the computation of the scattered radiation is optionally applied for each of the acquired projections at each gantry rotation angle. Optionally, in order to save processing time, the computation of the scattered radiation is done only at particular projection angles and the data acquired at other projection angles is corrected by subtracting an estimated correction based on interpolation between measurements at said particular projection angles. Further optionally, scatter data measured at multiple projection angles may be smoothed as a function of projection angle prior to subtraction of the scattered radiation in order to reduce statistical error.

In non-CT imaging systems such as digital radiography, computed radiography and fluoroscopy, data is typically acquired at a single source-subject-detector geometry at a time. In single image systems such as digital radiography the single set of data acquired according to the present invention contains the information needed to deduce and subtract the scattered component according to the procedure described herein above. In dynamic imaging systems such as fluoroscopy or angiography systems multiple images are taken at same or substantially same geometry. Assuming changes in the subject are slow, e.g. slow change in catheter position or slow movement of the subject, the scattered radiation component may be measured once and used for correction of subsequent images or the measured scattered radiation may be averaged over subsequent acquisitions for more accurate subtraction.

Figure 4A:
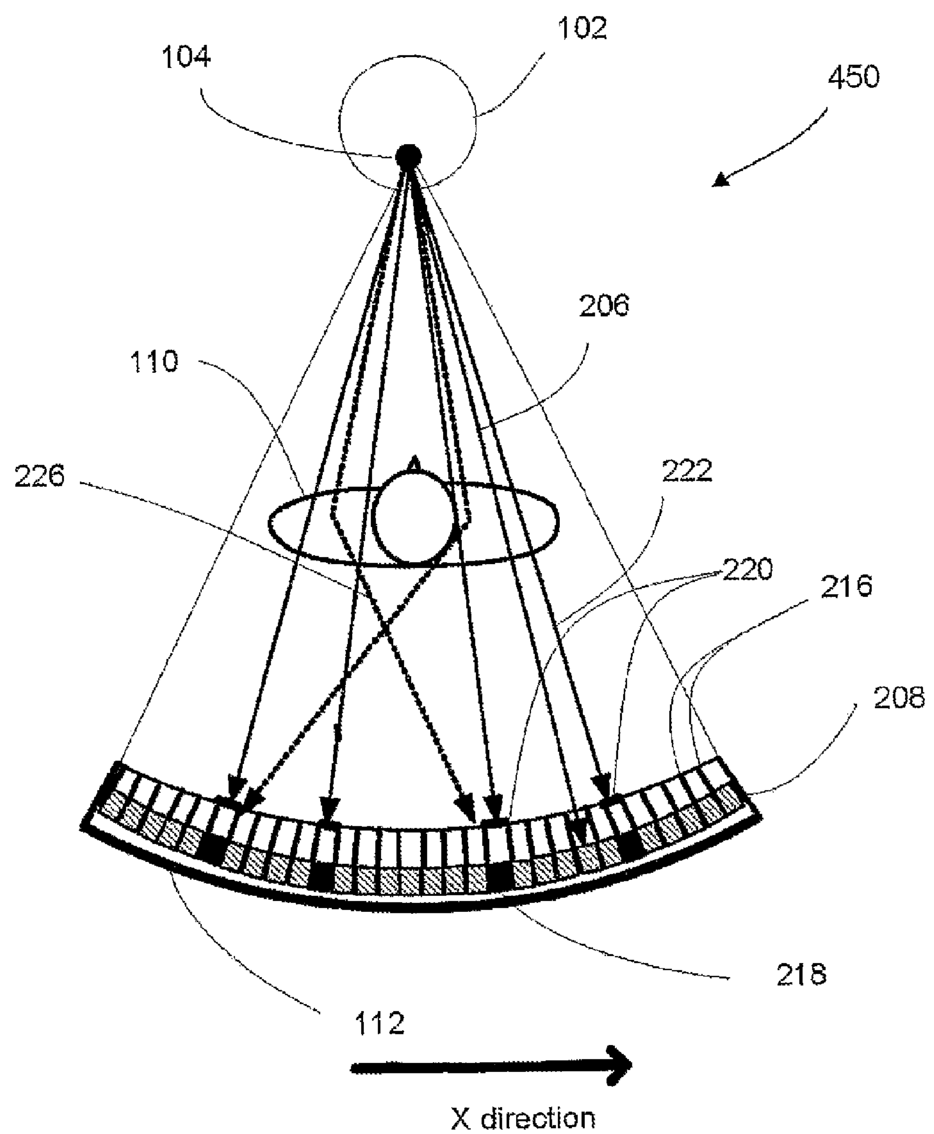
FIG. 4*a* schematically depicts a front view of a CT system 450 according to an exemplary embodiment of the invention, in which the detector array is fitted with anti-scatter grid array.

FIG. 4a schematically depicts a front view of a CT system 450 according to an exemplary embodiment of the invention, in which the detector array 208 is fitted with antiscatter grid array 216. Antiscatter grid array 216 is preferably composed of radiation opaque foils that may be interleaved with radiation translucent spacers, all assembled together by methods known in the art. In the embodiment of FIG. 4*a* shields 220 are positioned directly on top of the anti-scatter assembly and are aligned to shade specific, desired detector elements or part thereof (shown darkened in the figure). Assuming the antiscatter grid array 216 is one-dimensional with the leafs parallel to the Z axis (detector column direction), much of the scattered radiation in the azimuthally direction (X,Y plane) is absorbed by the antiscatter grid as shown in FIG. 4*a* for a scattered ray marked by numeral 226. Detector elements shaded by shields 220 are subject mostly to radiation scattered in the direction of the corresponding detector column. For clarity, direct radiation 206 arrives at detector array 208.

Figure 4B:
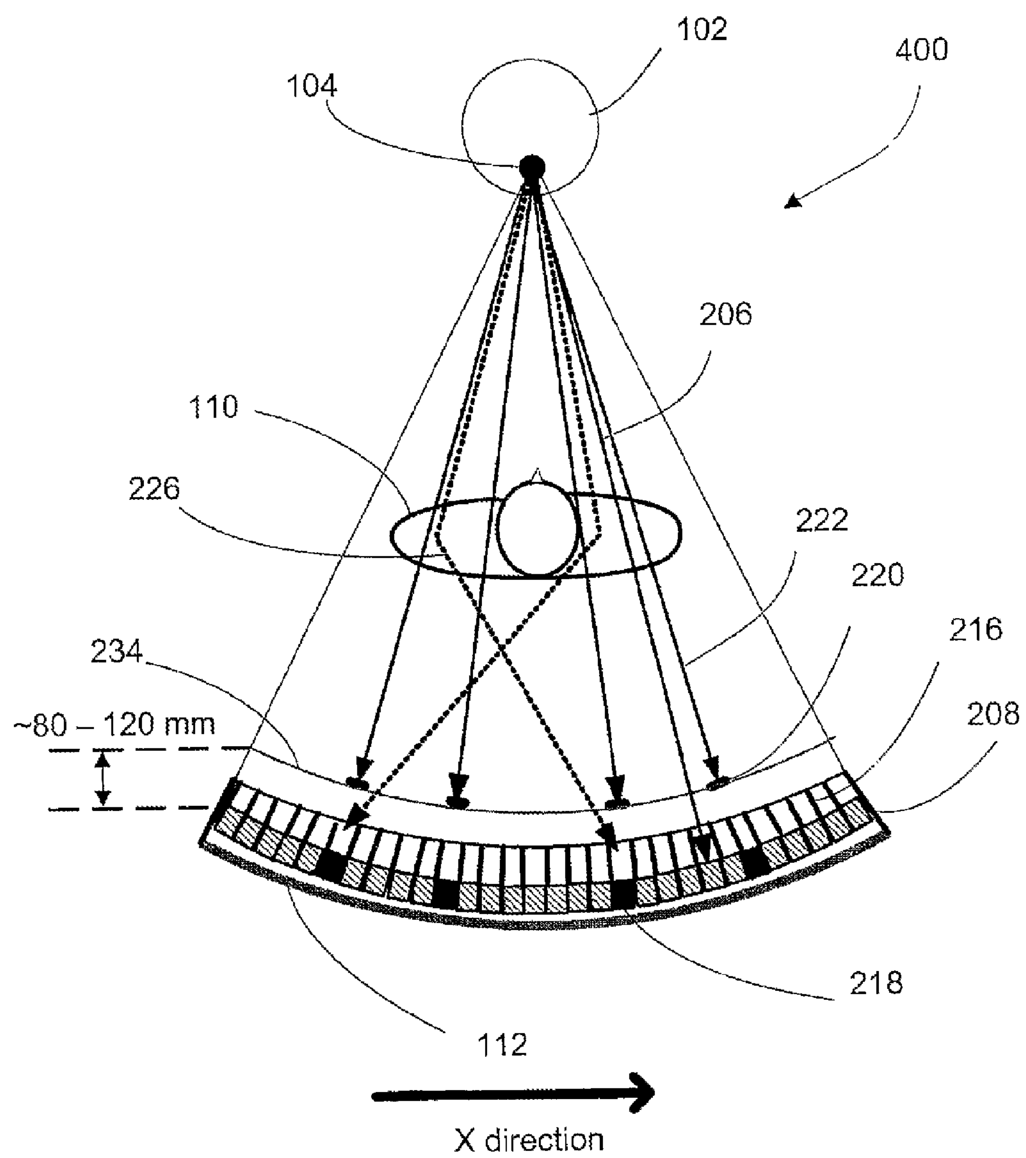
FIG. 4*b* schematically depicts a front view of a CT system 400 in which the detector array is provided with anti-scatter grid and an outer radiation translucent arc shaped cover, according to an exemplary embodiment of the current invention.

FIG. 4*b* schematically depicts a front view of a CT system 400 in which detector array 208 is provided with anti-scatter grid array 216 and outer radiation translucent arc shaped cover 234, according to an exemplary embodiment of the current invention. For clarity, direct radiation 206 arrives at detector array 208.

Shields 220 are embedded in, or glued onto outer cover 234, above the anti-scatter grid array 216, and are aligned to shade specific detector elements or part thereof (shown darkened in this figure). The distance of the shields 220 from the detector array 208 may be in the range of 80 mm to 120 mm although a lower or higher distance can be used too. The shields mounting arrangement of this embodiment is convenient in systems wherein there is a one dimensional antiscatter grid array of a relatively short height (e.g. 5 mm to 20 mm) or there is a two-dimensional grid. In this embodiment, shaded detector elements receive radiation scattered azimuthally as well as out of the plane more efficiently than shaded detector elements in the embodiment of FIG. 4*a*. Therefore, in this embodiment shaded detector elements present a more accurate measurement of the total scattered radiation received by un-shaded elements.

Figure 4C:
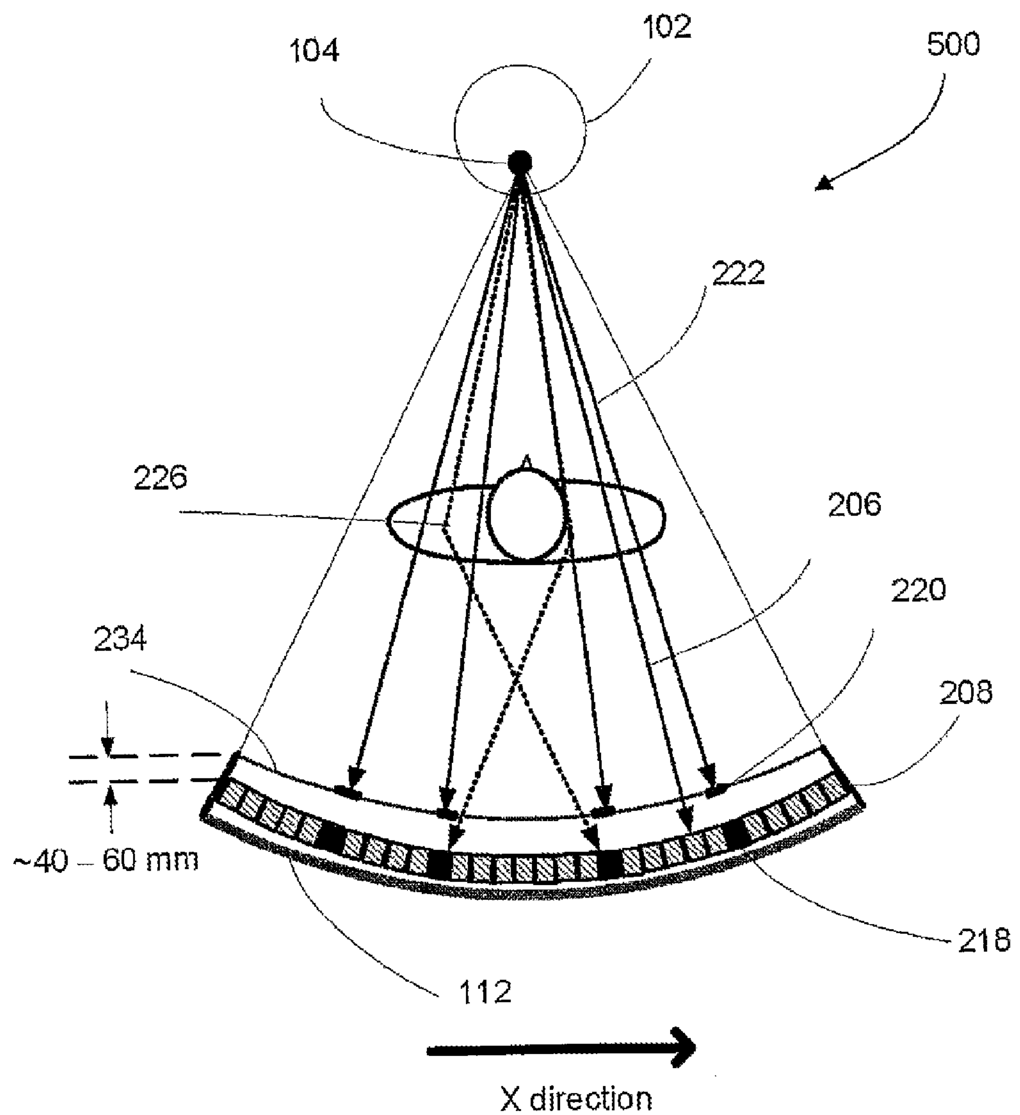
FIG. 4*c* schematically depicts a front view of a CT system 500 according to an exemplary embodiment of the current invention in which the shields are positioned on the outer cover of the detectors array and no anti-scatter grid is provided.

FIG. 4*c* schematically depicts a front view of a CT system 500 according to an exemplary embodiment of the current invention in which the shields are positioned on the outer cover 234 of the detectors array and no antiscatter grid is provided.

In this embodiment, a high degree of scattered radiation is received by the detector array 208 and scatter correction as provided by using shaded detector elements (shown darkened in this figure) is particularly useful.

Figure 5A:
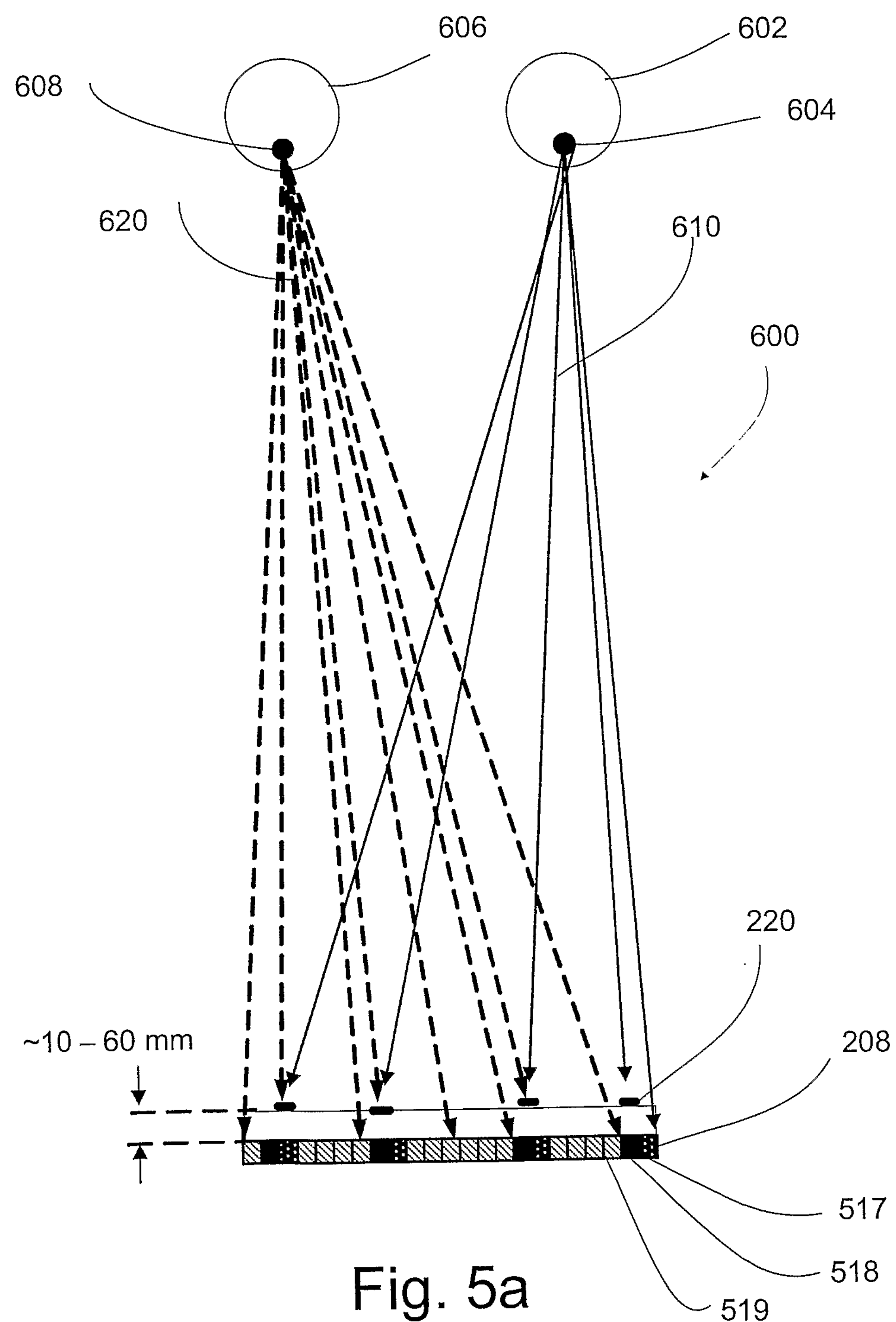
FIG. 5*a* schematically depicts a view of a CT system 600 comprises of more than one X-ray source according to yet another exemplary embodiment of the current invention.

FIG. 5*a* schematically depicts a view of a CT system 600 comprises of more than one X-ray source according to yet another exemplary embodiment of the current invention.

In the depicted example, two x-ray sources (602 and 606 having focal points 604 and 608, respectively) displaced from each other along the Z axis are shown by a way of a non-restrictive example. In other embodiments more than two x-ray sources may be provided. The multiple x-ray sources may be displaced from each other also in other directions or form an array. In system 600, the multiple x-ray sources irradiate a common detector array 208. The x-ray sources 602 and 606 may be activated alternatively at a high switching rate.

Radiation shields 220 are positioned such that they block the direct radiation from each x-ray source to a particular set of detector elements, wherein the set of shaded detector elements is different for each x-ray source. Further, the detector elements which are shaded from direct radiation of one x-ray source are operable to receive the direct radiation from at least one other x-ray source.

For example, detector element 517 is shielded from x-ray source 608, but not shielded from x-ray source 602. In contrast detector element 518 is shielded from x-ray source 602 but not from x-ray source 606, while detector elements 519 are not shielded from any x-ray source. Optionally, some detector elements may be shielded from both x-ray sources. In the depicted embodiment, detector elements 517 and 518 are depicted adjacent. However, depending on the size of detector elements, size of shields, distance from shields to detector elements and the angular separation between x-ray sources (as seen from the detector elements), a plurality of detector elements 517 or 518 may be contiguous, and detector elements 517 and 518 may be separated by one or few detector elements 519.

Figure 5B:
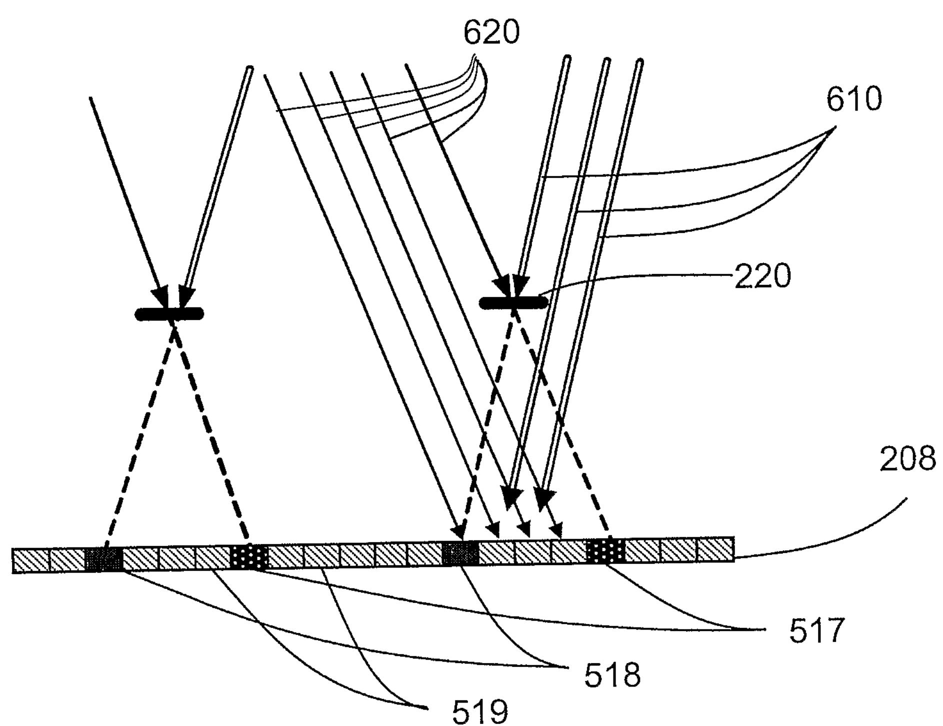
FIG. 5*b* schematically depicts "zoom-in" view of a detector array of a CT system 600 comprises of more than one X-ray source according to yet another exemplary embodiment of the current invention.

FIG. 5*b* schematically depicts "zoom-in" view of a detector array of a CT system 600 comprises of more than one X-ray source according to the exemplary embodiment of the current invention.

For example, in the detector array 208 shown in FIG. 5*b* detector elements 518 are shaded from direct radiation 610 of one x-ray source and receive direct radiation from a second x-ray source 606, and detector elements 517 are shaded from direct radiation 620 of the second x-ray source 606 and receive direct radiation 610 from the first x-ray source (the x-ray sources are not shown in the figure). This arrangement provides a simple way to calibrate and normalize the shaded detectors elements wherein a detector from one x-ray source is calibrated by radiation emitted by other x-ray sources.

Multiple X ray sources such as shown in FIG. 5*a* may be provided as separate X ray source assemblies (shown in FIG. 5*a*) or as an integrated X ray source with multiple focal spots.

In some embodiments, multiple X ray sources have multiple detector arrays associated with them or have different areas of a common detector array responsive to radiation from different sources. In such embodiments different sets of shield are provided for each of the multiplicity of detectors or active detector areas.

In some embodiments scatter correction based solely on measurement of scattered radiation by shaded detector elements and computation of the scattered versus direct components of the radiation received by a detector array as described hereinabove. In other embodiments scatter correction is based on measurements by shaded detector elements combined with other scatter calibration methods and correction algorithms known in the art.

Preferred embodiments are described by a way of a non restrictive example as using pixilated detector arrays with discrete detector elements. However, the invention applies also to detector arrays without discrete elements, wherein a limited area or multiple limited areas of the array may be shaded, or to detector array with small elements (e.g. below 1 mm) wherein groups of detector elements may be fully or partially shaded by shields.

Further, preferred embodiments are described by a way of non restrictive examples as using a rotating gantry which carries the X ray source or sources and detector array (known in the art as third generation CT). However, the invention applies also to CT wherein the detector array is static (known in the art as fourth generation CT), the X ray source is made to move by electronic rather than mechanical means (known in the art as electron beam CT) and cone beam CT with circular or non-circular focal spot trajectories.

Further, preferred embodiments are described by a way of non restrictive examples as applicable to CT imaging. However, the invention applies also to projection X ray imaging wherein area detectors of different types are used to image X rays with or without antiscatter grid. Such systems including Digital Radiography, Computed Radiography, Fluoroscopy and other systems can benefit from scatter correction using the present invention as well.

Further, preferred embodiments are described by a way of non restrictive examples as applicable to medical imaging. However, the invention applies also to non medical imaging of non-human subjects such as non-destructive testing and homeland security imaging.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A method for imaging a subject while correcting scattered radiation scattered from the subject, the method comprising:

providing at least a first source of X ray radiation, a detector for the X ray radiation, and a plurality of radiation shields, wherein said plurality of radiation shields is positioned between the first source of x-ray radiation and the detector;

irradiating the subject by said first source of X ray radiation and acquiring X ray data from said detector, wherein X rays received by said detector comprise: direct radiation from the first source of x-ray radiation that was attenuated by the subject, and scattered radiation that was scattered by the subject, and wherein shielded parts of a detector area are shaded by said plurality of radiation shields such that said shielded parts are responsive to direct radiation and responsive to scattered radiation, and wherein un-shielded pans of the detector area are responsive to direct radiation and to scattered radiation;

correcting the X ray data received by said un-shielded parts of the detector area, wherein correcting scattered radiation is based on scattered radiation data received by said shielded parts of the detector area; and correcting the X ray data received by said shielded pads of said detector area, wherein correcting scatterred radiation is based on direct radiation data received by said unshielded parts of the detector area.

2. The method of claim 1 wherein said first source of X ray radiation, said detector, and said plurality of radiation shields are mounted on a rotating frame and operative for computer tomography imaging of the subject.

3. The method of claim 2, wherein correction of scattered radiation is applied to multiple X ray projection data, each projection data acquired at a different one of multiple rotation angles.

4. The method of claim 1, further comprising using said first source of X ray radiation, said detector and said plurality of radiation shields for a fluoroscopic imaging of the subject.

5. The method of claim 1, wherein said detector is pixilated to detector elements and said plurality of radiation shields comprise elements of radiation opaque material blocking substantially all direct radiation from reaching shielded detector elements.

6. The method of claim 1, wherein said detector is pixilated to detector elements and said plurality of radiation shields comprise radiation opaque material blocking substantially all direct radiation from reaching a part of an active area of partially shielded detector elements.

7. The method of claim 1, further comprising moving said plurality of radiation shields out of the beam path during a calibration process of said detector, and into the beam path during imaging of the subject,

8. A method of claim 7, wherein the step of the correction of scatterred radiation comprises correction of data acquired at one time based on scattered radiation measured at a different time.

9. A method of claim 7, wherein the array of shields is operable to move between alternate positions during the calibration process such that parts of the detector which are shielded during subject imaging are not shielded during calibration.

10. The method of claim 1, and further comprising, providing an anti-scatter grid adjacent to said detector and wherein said plurality of radiation shields are positioned adjacent to said anti-scatter grid.

11. The method of claim 10 wherein said anti-scatter grid is adjacent to said detector and said plurality of radiation shields are positioned, at a distance from the antiscatter grid, posterior to the subject.

12. The method of claim 1, wherein said plurality of radiation shields are positioned at a distance from a surface of said detector, posterior to the subject.

13. The method of claim 1, and farther comprising providing a second X ray source, displaced from said first source of X ray radiation, wherein said first source of X ray radiation and said second X ray sources are operable to irradiate a common area of said detector, wherein said plurality of radiation shields are operable to shield direct radiation from said first source of X ray radiation from reaching shielded parts of said detector, and wherein said shielded parts of said detector are capable to receive direct radiation from said second X ray source.

14. The method of claim 13, further comprising using direct radiation received from said second X ray source for calibrating detector elements which are shielded by said plurality of radiation shields from radiation emitted by said first source of X ray radiation and wherein said detector is pixilated to detector elements.

15. The method of claim 13, and farther comprising operating said first source CA X ray radiation and said second X ray sources sequentially.

16. The method of claim 1, wherein said detector is pixilated to detector elements and wherein the step of correcting the data received, by said un-shielded parts of the detector area comprises:

calculating an amount of scattering received by detector elements from data acquired by said shielded parts of said detector; and subtracting said calculated amount of scattering from the data acquired by said un-shielded parts of said detector.

17. The method of claim 1, wherein the step of correcting the data received by said un-shielded parts of the detector area comprises fitting a scatter map for the detector area based on the read out of said shielded parts of said detector.

18. The method of claim 17, wherein the step of fitting a scatter map for the detector area comprises using a polynomial fitting function.

19. The method of claim 17, wherein the step of fitting a scatter map for the detector area comprises performing spatial interpolation on read out of shielded pans of said detector.

20. The method of claim 19, wherein the step of performing spatial interpolation comprises using cubic or higher order spline interpolation.

21. A method of claim 1, wherein the process of the correction of scattered radiation comprises averaging of scatter data measured by shielded parts of said detector over time.

22. The method of claim 1, wherein said detector is pixilated to detector elements and the step of correcting the data received by shielded parts of an area of the detector comprises interpolation of scatter corrected data receieved by un-shielded detector elements.

23. The method of claim 1 wherein the step of correcting, the data received by shielded parts of an area of the detector comprises normalization of scattered corrected data receieved by said shielded parts according to the shielded fraction of said shielded parts.

24. A system for imaging a subject while correcting scattered radiation, the system comprising:

at least one first source of X-ray radiation;

a detector for detecting said X-ray radiation;

an array of radiation shields, said array of radiation shields being positioned between said at least one first source of X-ray radiation and said detector;

a controller configured for acquiring X-ray data from said detector, wherein X-rays received by said detector comprise direction radiation from the at least one first source of X-ray radiation that was attenuated by a subject and scattered radiation that was scattered by the subject, and wherein parts of a detector area are shielded by the array of radiation shields and are substantially irresponsive to said direct radiation and responsive to said scattered radiation and the parts of the detector area that are unshielded are responsive to direction radiation and to scattered radiation; and an image processor configured for correcting the X-ray data received by the parts of the detector area which are not shielded by the array of radiation shields, wherein a correction is based on scattered radiation data received by the parts of the detector area which are shielded by the array of radiation shields, wherein said image processor further configured for correcting the X-ray data received by said parts of the detector area which are shielded by the array of radiation shields, wherein a correction is based on direction radiation data received by the parts of said detector area which are not shielded by the array of radiation shields.

25. The system of claim 24, and further comprising a rotating frame, Wherein said at least one X ray source, said detector and said array of radiation shields are mounted on the rotating frame and operative for computer tomography imaging of the subject.

26. The system of claim 25, wherein correction of scatterred radiation is applied to multiple X ray projection data, each projection data acquired at a different one of multiple rotation angles.

27. The system of claim 24, wherein said at least one first source of x ray radiation, said detector and said array of shields are used for is single radiographic imaging of the subject.

28. The system of claim 24, wherein said at least one first source of x ray radiation, said detector and said array of shields are used for fluoroscopic imaging of the subject.

29. The system of claim 24, wherein said detector is pixilated to detector elements and said array of radiation shields comprised of elements of radiation opaque material blocking substantially all direct radiation from reaching shielded detector elements.

30. The system of claim 24, wherein said detector is pixilated to detector elements and said array of radiation shields comprised of radiation opaque material blocking substantially all direct radiation from reaching a part of an active area of partially shielded detector elements.

31. The system of claim 24, wherein said array of radiation shields is operable to move out of a beam path during calibration process and move into the beam path during imaging of the subject.

32. the system of claim 24, and further comprising an anti-scatter grid positioned adjacent to said detector, wherein said array of radiation shields comprising elements of radiation opaque material arc positioned adjacent to said anti-scatter grid.

33. The system of claim 24, and further comprising an anti-scatter grid positioned adjacent to said detector and said array of radiation shields comprising elements of radiation opaque material are positioned at a distance from said anti-scatter grid, posterior to the subject.

34. The system of claim 24, wherein said array of radiation shields comprising elements of radiation opaque material are positioned at a distance from said detector's face, posterior to said subject.

35. The system of claim 24, and further comprising at least one second source of x ray radiation displaced from said at least one first source of x ray radiation, wherein said at least one first source of x ray radiation and said at least one second source of x ray radiation are operable to irradiate a common detector area., wherein the array of radiation shields are operable to Shield direct radiation from said at least one first source of x ray radiation from reaching shielded parts of said detector, said shielded parts capable of receiving direct radiation from said at least one second source of x ray radiation.

36. The system of claim 35, wherein direct radiation received from said at least one first source of x ray radiation is used for calibrating said detector elements which are shielded h said array of radiation shields from radiation emitted by a said at least one second X ray source.

37. The system of claim 24, wherein said detector is pixilated to detector elements and correcting the data received by parts of the detector area which are not shielded by said array of radiation shields comprises:

calculating an amount of scattering received by detector elements which are not shielded by said array of radiation shields, by interpolation of data received by said shielded parts of said detector, and subtracting said calculated amount of scattering from the data acquired by said un-shielded parts of said detector.

38. The system of claim 24, wherein said array of radiation shields is operable to move between alternate positions during a calibration process such that parts of said detector which are shielded during imaging the subject are not shielded during calibration.

39. The system of claim 24, wherein said array of radiation shields is operable to move, between at least first and second calibration positions during a calibration process such that parts of said detector which are shielded while said array of radiation shields in said first calibration position are not shielded while said array of radiation shields in said second calibration position.

40. The system of claim 24, wherein said detector is pixilated to detector elements and correcting the data received by Shielded parts of an area of the detector comprises interpolation of scatter corrected data receieved by an-shielded detector elements.

41. The system of claim 24, wherein correcting the data received by shielded, parts of an area of the detector comprises normalization of scattered corrected data receieved by said shielded parts according to the shielded fraction of said shielded parts.

* * * * *